United States Patent
Hauptmann et al.

(10) Patent No.: US 11,375,328 B2
(45) Date of Patent: Jun. 28, 2022

(54) EXTENDED BANDWIDTH HEARING AID WITH DYNAMICALLY ADJUSTABLE SAMPLING RATE FOR POWER OPTIMIZED DEPLOYMENT OF COORDINATED RESET (CR) NEUROMODULATION FOR THE TREATMENT OF SUBJECTIVE TONAL TINNITUS

(71) Applicant: Aureliym GmbH, Bad Neuenahr-Ahrweiler (DE)

(72) Inventors: Christian Hauptmann, Starnberg (DE); Markus Haller, Beirut (LB); Mark Williams, London (GB); Niklaus Burger, Köniz (CH); Jean-Noël Fehr, Neuchatel (DE); Urs Anliker, Frauenkappelen (CH); Sven Grob, Düseldorf (DE)

(73) Assignee: Aurelium GMBH, Bad Neuenahr-Ahrweiler (DE)

( * ) Notice: Subject to any disclaimer, the term of this patent is extended or adjusted under 35 U.S.C. 154(b) by 363 days.

(21) Appl. No.: 16/477,076

(22) PCT Filed: Jan. 10, 2018

(86) PCT No.: PCT/EP2018/050530
§ 371 (c)(1),
(2) Date: Jul. 10, 2019

(87) PCT Pub. No.: WO2018/130552
PCT Pub. Date: Jul. 19, 2018

(65) Prior Publication Data
US 2019/0342679 A1    Nov. 7, 2019

Related U.S. Application Data

(60) Provisional application No. 62/444,751, filed on Jan. 10, 2017.

(51) Int. Cl.
| H04R 25/00 | (2006.01) |
| A61N 1/08 | (2006.01) |
| A61N 1/372 | (2006.01) |

(52) U.S. Cl.
CPC .............. *H04R 25/75* (2013.01); *A61N 1/08* (2013.01); *A61N 1/37217* (2013.01);
(Continued)

(58) Field of Classification Search
None
See application file for complete search history.

(56) References Cited

U.S. PATENT DOCUMENTS

2010/0054510 A1    3/2010  Schumaier
2015/0297444 A1*  10/2015 Tass ..................... A61N 5/0622
                                                        601/47
2017/0347213 A1*  11/2017 Goorevich ............. H04R 25/43

OTHER PUBLICATIONS

International Search Report and Written Opinion issued in International Application No. PCT/EP18/50530 dated Mar. 6, 2018.
(Continued)

*Primary Examiner* — Kenny H Truong
(74) *Attorney, Agent, or Firm* — Quinn IP Law

(57) ABSTRACT

A hearing aid device is provided. The hearing aid device comprises: an input unit configured to receive an acoustical input and transform it into an electrical input signal; a signal transforming unit coupled to the input unit and configured to process the electrical input signal to obtain an electrical output signal; a stimulation unit configured to generate a stimulation signal for acoustic coordinated reset neuromodulation therapy; an output unit configured to transform at least one of the electrical output signal and the stimulation signal into an acoustical output.

13 Claims, 4 Drawing Sheets

(52) U.S. Cl.
CPC ......... *A61N 1/37282* (2013.01); *H04R 25/30* (2013.01); *H04R 25/70* (2013.01); *H04R 2460/03* (2013.01)

(56) References Cited

OTHER PUBLICATIONS

Gerta Rucker, 11 Reply to Tass et al. on "Counteracting tinnitus by acoustic coordinated reset neuromodulation" Restorative neurology and neuroscience, vol. 30 (2). 2012, Restorative neurology and neuroscience, Jan. 1, 2013, pp. 233-234, XP055456502, Netherlands.

Deutsche Tinnitus-Liga e.V. . . . "Deutsche Tinnitus-Liga e.V.-Nachrichten zur akustischen CR-Ne", Nov. 5, 2015, XP055456584.

\* cited by examiner

EXTENDED BANDWIDTH HEARING AID WITH DYNAMICALLY ADJUSTABLE SAMPLING RATE FOR POWER OPTIMIZED DEPLOYMENT OF COORDINATED RESET (CR) NEUROMODULATION FOR THE TREATMENT OF SUBJECTIVE TONAL TINNITUS

FIELD OF THE INVENTION

Various embodiments of the systems, devices, components and methods disclosed and described herein relate to hearing aid and acoustic coordinated reset neuromodulation therapies delivered to patients via the hearing aid.

BACKGROUND

Acoustic coordinated reset (CR) neuromodulation therapy is a form of noninvasive neuromodulation therapy for treating primary tinnitus, in particular, the frequency-specific, often tonal, tinnitus commonly seen in these patients. See, for example, "Counteracting tinnitus by acoustic coordinated reset neuromodulation", Restor. Neurol. Neurosci. 30(2):137-159. Tass et al., 2012.

Many patients with tinnitus also suffer from hearing loss and hence require hearing aids for most of their daily listening activities. Hearing aids need to provide a good performance in terms of battery consumption because of their continued use and small dimensions. The latest hearing aids can receive stream signals, e.g. using Bluetooth technology, via gateway devices called streamers or directly in the case of Apple proprietary streaming protocol. Although both methods manage to reduce the power supply required by traditional Bluetooth, so that streaming signals is compatible with the power constraints of hearing aids, this wireless communication still weighs on the battery consumption, reducing the duration of the battery in the hearing aid.

Further, hearing aids are nowadays digital and the signal processing inside the hearing aids is tuned for a frequency bandwidth up to 5-8 kHz in most cases, and up to 10 kHz in high-end hearing aids. This means, in particular, that the sampling rate in the digital signal processing (e.g. for analog-to-digital (A/D) converters and digital-to-analog (D/A) converters) is around 10-16 kHz. Indeed, the Nyquist-Shannon sampling theorem requires the sampling to be at least double that of the maximum component frequency of the function being sampled.

Currently CR neuromodulation for the treatment of subjective tonal tinnitus uses sound output stages with frequencies of up to 20 kHz. Accordingly, a higher sampling rate, up to 40 kHz, is needed for processing CR stimulation signals. However, processing more samples involves more computational work and, therefore, consumes more processor power and results in reduced battery duration of the device used to deliver the CR neuromodulation.

Thus, streaming CR neuromodulation signals to a hearing aid poses several challenges in terms of battery consumption as well as quality, and thus, efficacy of the delivered CR neuromodulation signals. It is therefore a problem to provide a device for a patient affected both by tinnitus and hearing loss, which can efficiently function as hearing aid and for providing CR neuromodulation signals.

SUMMARY

In one aspect, the invention provides a hearing aid device that is adapted to apply a CR stimulation signals to a user's ear. The hearing aid device comprises an input unit configured to receive an acoustical input and transform it into an electrical input signal. In particular, the input unit may receive sound waves of an environmental sound as the acoustical input and transforms it into an electrical signal in which the voltage varies with time. The input unit may comprise a transducer, such as a microphone, for the transformation of the acoustic signal to the electric signal. Moreover, the input unit preferably further comprises an A/D converter. While the transducer may transform the sound wave into an analog electrical input signal, in which the instantaneous voltage varies continuously with time in correspondence to the pressure of the sound wave. The A/D converter may receive the analog electrical input signal and turns it into a digital electrical input signal, which has a discrete number of voltage values at given times.

Moreover, the hearing aid device comprises a signal transforming unit which is directly or indirectly coupled to the input unit such that it receives the (preferably digital) electrical input signal and which is configured to process the electrical input signal to obtain an electrical output signal. In other words, the signal transforming unit is coupled to the input unit, in the sense that it is connected to the input unit such that it can receive the digital electrical input signal. The signal transforming unit processes the digital electrical input signal and produces the output signal, which preferably is also a digital signal. The signal transforming unit is specifically adapted to process the electrical input signal in accordance with a (preferably user-specific) hearing aid functionality. Thus, the signal transforming unit may at least partially (e.g. time-wise and/or depending on a frequency and or amplitude of the original acoustic input signal) amplify the (digital) electrical input signal. Exemplarily, the amplification may be performed on the basis of user data defining the hearing impairment in the user, e.g. the hearing threshold at given frequencies. These data may be stored in a memory within the hearing aid device, wherein the memory may be a component of the signal transforming unit itself or may be external to it. Additionally or alternatively to the amplification, other modifications of the digital electrical input signal may be performed, such as noise suppression or filtering. The digital electrical output signal produced by the signal transforming unit is then sent to an output unit coupled to the signal transforming unit.

Furthermore, specific to an aspect of the present invention, the hear aid device comprises a stimulation unit configured to generate a stimulation signal suitable for acoustic coordinated reset (CR) neuromodulation therapy. In particular, the stimulation signal is an electrical signal that can be later converted into an acoustic wave perceivable by a patient and suitable for treating tinnitus. The stimulation unit may generate the same stimulation signal at different times or different stimulation signals at different times, wherein the different stimulation signals may have different characteristics, e.g. they may define different frequencies and/or different timbres and/or different amplitudes and/or different durations/lengths. The stimulation signal may be any of a sinusoidal signal, a narrow bandwidth signal, a noisy signal and other kind of signals and it is preferably created also as a digital signal. The one or more stimulation signals may be generated on the basis of data related to the tinnitus, such as tinnitus pitch, intensity and/or timbre. The tinnitus data and the stimulation parameters, including e.g. duration of the stimulation, may be stored in a memory within the hearing aid device, wherein the memory may be a component of the stimulation unit itself or may be external to it.

Moreover, the hearing aid device comprises an output unit configured to transform the electrical output signal and the stimulation signal into an acoustical output. Specifically during a period when applying a CR therapy signal, the output unit may even receive the electrical output signal and the stimulation signal simultaneously and transform the combination of both signals as an acoustical output in which a (partially) amplified acoustical input signal (for the hearing aid functionality) is superposed with an acoustical therapy signal.

The output unit may be at least coupled (directly) to the signal transforming unit such as to receive the (digital) electrical output signal directly from the signal transforming unit. Thus, the output unit can transform the digital electrical output signal into a respective acoustical output, i.e. a sound wave, to perform the desired hearing aid functionality. Preferably symmetrically to the input unit, the output unit may comprise at least one D/A converter for converting the digital electrical output signal into a respective analog signal and a transducer, such as a loudspeaker, for turning the analog electrical signal into an acoustic wave.

According to some examples, the output unit may be directly coupled to the stimulation unit and may receive the (preferably digital) stimulation signal directly from the stimulation unit. Thus, the output unit can transform the electrical stimulation signal into a respective acoustical stimulation signal, i.e. a sound wave, to perform the desired CR therapy functionality. In particular, in one embodiment the output unit may receive the digital stimulation signal at the at least one D/A converter for converting the digital stimulation signal into a respective analog signal. The transducer may then turn the analog electrical stimulation signal into an acoustic wave. In another embodiment, the output unit may comprise a second D/A converter in additional to the first D/A converter for converting the digital stimulation signal into a respective analog signal. The analog output signals of the first and second D/A converters may then be turned into respective acoustic waves by dedicated separate transducers or by the same transducer.

According to other examples, the stimulation unit may be coupled to the signal transforming unit such that the signal transforming unit receives and processes the (digital) stimulation signal. The signal transforming unit may transform the (digital) stimulation signal, e.g. on the basis of the hearing impairment data and/or in relation to an input signal concurrent to the stimulation signal. For example, the intensity of the stimulation signal may be adjusted depending on the input signal. In these cases, the signal transforming unit may generate a combined electrical output signal based on the (processed) electrical input signal and the received stimulation signal. The output unit receives the transformed digital stimulation signal (e.g. included in the combined electrical output signal) from the signal transforming unit.

Thus, the hearing aid device according to the invention can both (e.g. at the same time) process environmental sounds e.g. by amplifying them, as a conventional hearing aid, and generate CR neuromodulation signals.

The CR neuromodulation therapy does not need to be delivered continuously at all times, rather only for a given interval of time per day, e.g. several hours per day all together, and with pauses within these stimulation intervals. In other words, the stimulation unit generates the stimulation signal according to a (preferably individual) temporal schedule that comprises periods in which no (digital) stimulation signal is generated. Accordingly, during a substantive part of the time, the output unit may only receive the digital electrical output signal but no stimulation signal. Conversely, the user may find himself in a very quiet environment where no non-negligible acoustical inputs are present and the output unit may receive only the digital stimulation signal to be converted into a therapy sound.

In all other circumstances, the output unit of the hearing aid device may transform both the digital electrical output signal and the digital stimulation signal into an acoustical output, which may, thus, be a combination or superposition of the two signals.

Thus, the hearing aid device as described above is capable of generating a new acoustic signal in addition to elaborating the environment sounds, without receiving this signal via wireless communication. It turned out that generating the stimulation signal through a stimulation unit being integral part of the hearing aid device is more energy-efficient than receiving it from an external device via Bluetooth. Further, the generated signal is suitable for CR neuromodulation therapy, so that the treatment can be comfortably and easily delivered to a patient suffering from tinnitus and hearing impairment through the hearing aid that the patient has to wear in any case.

In some cases, a patient may wear two hearing aid devices, one per each ear, because he/she has a hearing impairment in both ears and/or because the CR neuromodulation therapy should be delivered to both ears. Accordingly, the first hearing aid device may be adapted for application to a left ear of a patient and the second hearing aid device may be adapted for application to a right ear of the patient.

The fact that the signal is generated within the hearing aid device and not streamed by an external source means that the stimulation signals generated respectively in the left and right hearing aid devices are not automatically synchronized. For example, a clock frequency that regulates the operations in circuits may be slightly different in the two hearing aid devices, although nominally being the same, due to inevitable imperfections in the production process. In order to address this issue, a synchronization signal may be used. In one example, the first hearing aid device (master device) is configured to send the synchronization signal to the second hearing aid device (slave device). In particular, the synchronization signal may be sent at fixed intervals, e.g. every second or every 10 second, and the slave device may adjust its operations on the basis of the timing coming from the master device. A processing unit in the master device may be configured to generate the synchronization signal and the slave device may comprise communication means to receive the signal.

In another example, the first hearing aid device and the second hearing aid device are configured to receive the synchronization signal from an external device. In this case, the synchronization signal may act as a calibration signal. The calibration signal may be sent twice to the hearing aid devices, with a predetermined time interval such as one second, between the first time and the second time. The hearing aid devices may be in a calibration mode, in which they measure how many clock cycles are contained in the predetermined time interval to obtain a calibration parameter. The calibration parameter may then be used when generating the stimulation signals with given frequencies. The calibration may be performed by a processing unit in the hearing aid devices.

The calibration signal may be sent wirelessly or via a wired connection to the hearing aid devices, which may comprise communication means to receive the signal.

Since a slight desynchronization between the two devices during operation is still acceptable and eventually not even noticeable for a user/patient, the (preferably wireless) communication between the two devices (and/or an external device) for synchronization can be significantly reduced as compared to the (wireless) communication needed for streaming the stimulation signal from an external source. Preferably, the synchronization signal may be sent at intervals not shorter than about one second, more preferably not shorter than about 10 seconds, even more preferably not shorter than about one minute. This can significantly reduce energy consumption in a device according this aspect.

As mentioned above, CR stimulation signals may have high frequency components, up to 20 kHz, which may not be accurately or at all reproduced by a conventional hearing aid output stage due to its conventionally low sampling rate. The output sampling rate for the output unit is, in particular, defined for the D/A converter in the output unit. In this context, the sampling rate may be a given positive integer number N of samples in the digital signal from which the analog signal is reconstructed. As explained above, the Nyquist-Shannon sampling theorem describes the relation between the sampling rate and the highest frequency of a signal, according to which signals reaching higher frequencies require a higher sampling rate. CR stimulation signals have high frequency components, e.g. higher than about 10 kHz or more generally up to 20 kHz. In contrast, the sounds usually processed by a hearing aid have a frequency that extends up to the range 5-8 kHz. Accordingly, a hearing aid device having also a CR therapy functionality may need to be operated at a sampling rate that is higher than the sampling rate typically used in normal/conventional hearing aids.

A digital signal, such as the digital electrical output signal and the digital stimulation signal, has, by definition, a discrete number of values at given times. The fraction of these values that is used to reconstruct an analog signal is, thus, the sampling rate. In particular, the sampling rate may correspond to the whole set of discrete values or it may be increased by upsampling. Upsampling entails creating a new set of values comprising the original values and interposing some zeros inbetween, then interpolating to replace the zeros. As a result, a higher number of samples including the original values and the interpolated ones, i.e. a higher sampling rate, is obtained.

The sampling rate of a D/A converter is limited by the update rate, i.e. the rate at which the D/A updates the output, which is usually equal to the clock rate of the processing unit divided by the number of clock cycles that it takes for the D/A to latch, including what is called settling time. Exemplarily, the D/A converter may employ delta-sigma modulation.

In a preferred implementation, the stimulation unit generates the stimulation signal according to a temporal schedule defining primary stimulation periods, in which no stimulation signal is generated (or in which the stimulation signal is generated having no frequency component higher than a primary threshold frequency), and secondary stimulation periods, in which the stimulation signal is generated (or in which the stimulation signal is generated with at least one frequency component higher than the primary threshold frequency). Preferably, the primary threshold frequency is not higher than about 10 kHz, more preferably not higher than about 8 kHz, even more preferably not higher than about 6 kHz, most preferably not higher than about 5 kHz.

Specifically in this aspect, the hearing aid device may further comprise a sampling rate controller, which may at least in some implementations also be called a clock cycle controller (or may implement clock cycle control functionalities) for reasons explained in more detail further below.

The sampling rate controller is preferably configured to set an output sampling rate for the output unit selected from a plurality of (preferably predefined) sampling rates including at least a primary sampling rate and at least one secondary sampling rate higher than the primary sampling rate, wherein the sampling rate controller is configured to set the primary sampling rate as the output sampling rate during the primary stimulation periods and to set the at least one secondary sampling rate as the output sampling rate during the secondary stimulation periods.

In other words, in this example, the hearing aid device comprises a sampling rate controller capable of modifying at least the output sampling rate of the output unit, so that a higher sampling rate is used only when necessary, namely when a CR stimulation signal with high frequency components is delivered to the patient.

Specifically, the sampling rate controller can set a sampling rate as one of a plurality of sampling rates including at least a primary sampling rate and at least one secondary sampling rate higher than the primary sampling rate. For example, the primary sampling rate may be not higher than about 30 kHz, preferably not higher than about 20 kHz, more preferably not higher than about 16 kHz, even more preferably not higher than about 12 kHz, most preferably not higher than about 10 kHz. Also, the at least one secondary sampling rate may be higher than about 12 kHz, preferably higher than about 16 kHz, more preferably higher than about 20 kHz, even more preferably higher than about 30 kHz, most preferably higher than about 40 kHz. The unit Hz is used for the sampling rate to indicate the number of samples per time unit.

Thus, according to this aspect the power consumption can be significantly reduced by efficiently adjusting the sampling rate of the output unit on the basis of the temporal schedule of the stimulation unit. Indeed, as already mentioned, the stimulation signals need only be delivered in given time windows and with pauses between consecutive signals. Accordingly, the sampling rate may be increased only when a stimulation signal is generated.

Further, the sampling rate may also be adjusted according to the characteristics of the stimulation signal, in particular its frequency components. As explained, the stimulation signal may be any of a sinusoidal signal, a narrow bandwidth signal, a noisy signal or other kind of signal. The frequency components of the stimulation signal combine to confer a characteristic frequency to the stimulation signal, which is chosen to lie in an interval around the tinnitus pitch.

If a tinnitus pitch is low, e.g. 4 kHz, the conventional sampling rate of a hearing aid may be sufficient for reproducing the acoustical wave corresponding to the different stimulation signals. If the tinnitus pitch is high, e.g. 8 kHz, the stimulation signals may include frequency components up to 12 kHz (or even higher), for example. Thus, the sampling rate needs to be increased in comparison to the conventional sampling rate only for some of the stimulation signals, namely those having higher frequency components.

When no stimulation signal is generated and the hearing aid device operates simply as hearing aid, the primary sampling rate is used. In some examples, the primary sampling rate may correspond to the number of samples originally present in the digital electrical output signal. In other words, the primary sampling rate may correspond to the sampling rate of the input unit, more specifically of the A/D converter. For an A/D converter, the sampling rate is a given positive integer number M of samples taken from the analog signal to form a digital signal. As explained above, the acoustical input received from the environment may be first processed by the A/D converter and then by the D/A converter. Accordingly, the sampling rate controller may set the primary sampling rate both as the input sampling rate for the input unit and as the output sampling rate for the output unit. Therefore, the sampling rate controller may set the primary sampling rate in the sense that it leaves the number of samples in the digital electrical output signal unvaried.

In other examples, the primary sampling rate may be different from the A/D converter sampling rate. Thus, the sampling rate controller may perform an upsampling or even a decimation to increase or decrease the sampling rate. Exemplarily, the sampling rate controller may set the primary sampling rate by upsampling the digital electrical output signal.

Similarly, the primary sampling rate is used when the generated stimulation signal has no frequency component higher than a primary threshold frequency.

Instead, in the secondary stimulation periods, the sampling rate controller may set one of the at least one secondary sampling rate as the output sampling rate.

In some examples, the digital stimulation signal may already be generated with a number of samples corresponding the secondary sampling rate, so that the sampling rate controller sets the secondary sampling rate in the sense that it leaves the number of samples in the digital stimulation signal unvaried. If at the same time a digital electrical output signal is being processed by the hearing aid device, the output unit applies the same secondary sampling rate to the digital electrical output signal. Given the high frequency nature of the stimulation signals in comparison to usual acoustical input, it may be advantageous to upsample the digital electrical output signal in order to reach the secondary sampling rate.

In other examples, the sampling rate controller may set the secondary sampling rate by upsampling the digital stimulation signal and, if present, the digital electrical output signal correspondingly.

As explained, switching from one sampling rate to the other enables the hearing aid device to save on the power consumption, while at the same time performing the double function of hearing aid and CR modulation delivery effectively.

In a further example, additional power may be saved by using a more refined sampling rate. The secondary stimulation periods may comprise at least first secondary stimulation periods, in which the stimulation signal is generated having at least one frequency component higher than the primary threshold frequency but no frequency component higher than a secondary threshold frequency, and second secondary stimulation periods, in which the stimulation signal is generated with at least one frequency component higher than the secondary threshold frequency. Correspondingly, the at least one secondary sampling rate may comprise a first secondary sampling rate and a second secondary sampling rate; and the sampling rate controller may be configured to set the first secondary sampling rate as the output sampling rate during the first secondary stimulation periods and to set the second secondary sampling rate as the output sampling rate during the second secondary stimulation periods.

Indeed, there may be more than two frequency regimes for the stimulation signal and, correspondingly, more than two output sampling rates, i.e. more than the primary sampling rate and one secondary sampling rate. Accordingly, a secondary threshold frequency, higher than the primary threshold frequency, may be introduced to further discriminate the stimulation signals according to their frequency components.

In particular, the secondary threshold frequency may be only a first secondary threshold frequency, whereas further frequency regimes may be defined according to a plurality of other secondary threshold frequencies, e.g. a second secondary threshold frequency, a third secondary threshold frequency and so on. The n-th secondary threshold frequency is higher than (n−1)th secondary threshold frequency. A corresponding secondary sampling rate is associated to each order of secondary stimulation periods.

Exemplarily, there may only one secondary threshold frequency besides the primary threshold frequency. The secondary threshold frequency may be higher than about 5 kHz, preferably higher than about 6 kHz, more preferably higher than about 8 kHz, most preferably higher than about 10 kHz.

Correspondingly, the primary sampling rate, the first secondary sampling rate and the second secondary sampling rate may be set by the sampling rate controller, wherein the first secondary sampling rate is lower than the second secondary sampling rate.

As already mentioned, during the primary stimulation periods, the sampling rate controller may set the primary sampling rate as the output sampling rate. In addition, during the first secondary stimulation periods, the sampling rate controller may set the first secondary sampling rate as the output sampling rate. Further, during the second secondary stimulation periods, the sampling rate controller may set the second secondary sampling rate as the output sampling rate.

Additionally or alternatively to the output unit, the sampling rate controller may be adapted to control a clock cycle for the signal transforming unit. Specifically in this implementation, the sampling rate controller may alternatively or also be called a clock cycle controller. The sampling rate controller (or clock cycle controller) may be configured to set a clock cycle rate for the signal transforming unit selected from a plurality of (preferably predefined) clock cycle rates including at least a primary clock cycle rate and at least one secondary clock cycle rate higher than the primary clock cycle rate, wherein the sampling rate controller is configured to set the primary clock cycle rate as the clock cycle rate for the signal transforming unit during the primary stimulation periods (specifically when no stimulation signal is generated) and to set the at least one secondary clock cycle rate as the clock cycle rate for the signal transforming unit during the secondary stimulation periods (specifically when the stimulation signal is generated.

Preferably, the stimulation unit is configured to generate the stimulation signal according to a temporal schedule defining passive stimulation periods, in which no stimulation signal is generated, and active stimulation periods, in which the stimulation signal is generated. In one example the passive stimulation periods may correspond or even be identical to the above mentioned primary stimulation periods, while the active stimulation periods may correspond or even be identical to the above mentioned secondary stimulation periods.

Again, the hearing aid device may comprises the clock cycle rate controller in addition to or instead of identical to the above mentioned sampling rate controller. In other words, a single controller (that may be called sampling rate controller or clock cycle controller) may be provided that controls either the sampling rate or the clock cycle rate or both. Alternatively, separate controllers may be provided simultaneously. Preferably, the clock cycle controller is configured to set a clock cycle rate for the signal transforming unit selected from a plurality of clock cycle rates including at least a primary clock cycle rate and at least one secondary clock cycle rate higher than the primary clock cycle rate, wherein the clock cycle rate controller is configured to set the primary clock cycle rate as the clock cycle rate for the signal transforming unit during the passive (or primary) stimulation periods and to set the at least one secondary clock cycle rate as the clock cycle rate for the signal transforming unit during the active (or secondary) stimulation periods.

Thus, according to this aspect the power consumption can be significantly reduced by efficiently adjusting the clock cycle rate for the signal transforming unit on the basis of the temporal schedule of the stimulation unit. In particular, only when a higher processing power is desired or needed in the signal transforming unit during a period where the stimulation signal is generated, a higher clock cycle rate is set of the signal transforming unit to properly process preferably both the hearing aid functionality without reduced quality and the CR therapy functionality. During the periods where no stimulation signal is generated, a lower processing power of the signal transforming unit may be sufficient and thus energy can be conserved.

In all the examples above, the sampling rate controller may be coupled to the stimulation unit in order to receive information about the temporal schedule, which may be stored in the memory of the stimulation unit, as mentioned above.

In one example, the hearing aid device may further comprise a tinnitus masker, i.e. a component that generates broad-band or narrow-band noise at low levels in order to mask the presence of tinnitus. The masking noise may be generated additionally or alternatively to the stimulation signal.

In another example, the transducer in the output unit of the hearing aid device may be adapted and configured to provide flatter and higher amplitude output signals at higher frequencies, using, for example, microelectromechanical systems (MEMS) technology.

In another aspect, the present invention provides a method for controlling a hearing aid device, the method comprising:
  receiving, at an input unit of the hearing aid device, an acoustical input and transforming it into an electrical input signal;
  processing, at a signal transforming unit of the hearing aid device coupled to the input unit, the electrical input signal to obtain an electrical output signal;
  generating, at a stimulation unit of the hearing aid device, a stimulation signal for acoustic coordinated reset neuromodulation therapy; and
  transforming, at an output unit of the hearing aid device, the electrical output signal and the stimulation signal into an acoustical output.

Preferably, the stimulation signal is generated according to a temporal schedule defining primary stimulation periods, in which no stimulation signal is generated or in which the stimulation signal is generated having no frequency component higher than a primary threshold frequency, and secondary stimulation periods, in which the stimulation signal is generated with at least one frequency component higher than the primary threshold frequency. In this respect, the method preferably further comprises setting (preferably at a sampling rate controller of the hearing aid device) an output sampling rate for the output unit selected from a plurality of sampling rates including at least a primary sampling rate and at least one secondary sampling rate higher than the primary sampling rate, wherein the primary sampling rate is set as the output sampling rate during the primary stimulation periods and the at least one secondary sampling rate is set as the output sampling rate during the secondary stimulation periods.

Preferably, the stimulation signal is generated according to a temporal schedule defining passive stimulation periods, in which no stimulation signal is generated, and active stimulation periods, in which the stimulation signal is generated. In this respect, the method preferably further comprises setting (preferably at a clock cycle rate controller of the hearing aid device) a clock cycle rate for the signal transforming unit selected from a plurality of clock cycle rates including at least a primary clock cycle rate and at least one secondary clock cycle rate higher than the primary clock cycle rate, wherein the primary clock cycle rate is set as the clock cycle rate for the signal transforming unit during the passive stimulation periods and the at least one secondary clock cycle rate is set as the clock cycle rate for the signal transforming unit during the active stimulation periods.

All details and explanations for a hearing aid device and its functionality as described herein are analogously applicable to the method according to preferred implementations of the invention. Therefore, according to preferred embodiments the method may specifically comprise alternative or additional operations or steps as describe herein as operations or functionalities of the hearing aid device.

DETAILED DESCRIPTION OF SOME EMBODIMENTS

Described herein are various embodiments of systems, devices, components and methods relating to hearing aid and acoustic coordinated reset neuromodulation therapies delivered to patients via the hearing aid.

FIG. 1 shows an example of a hearing aid device that can address hearing impairment and at the same time deliver CR neuromodulation therapy to a patient affected both by hearing loss and tinnitus.

Figure 1:
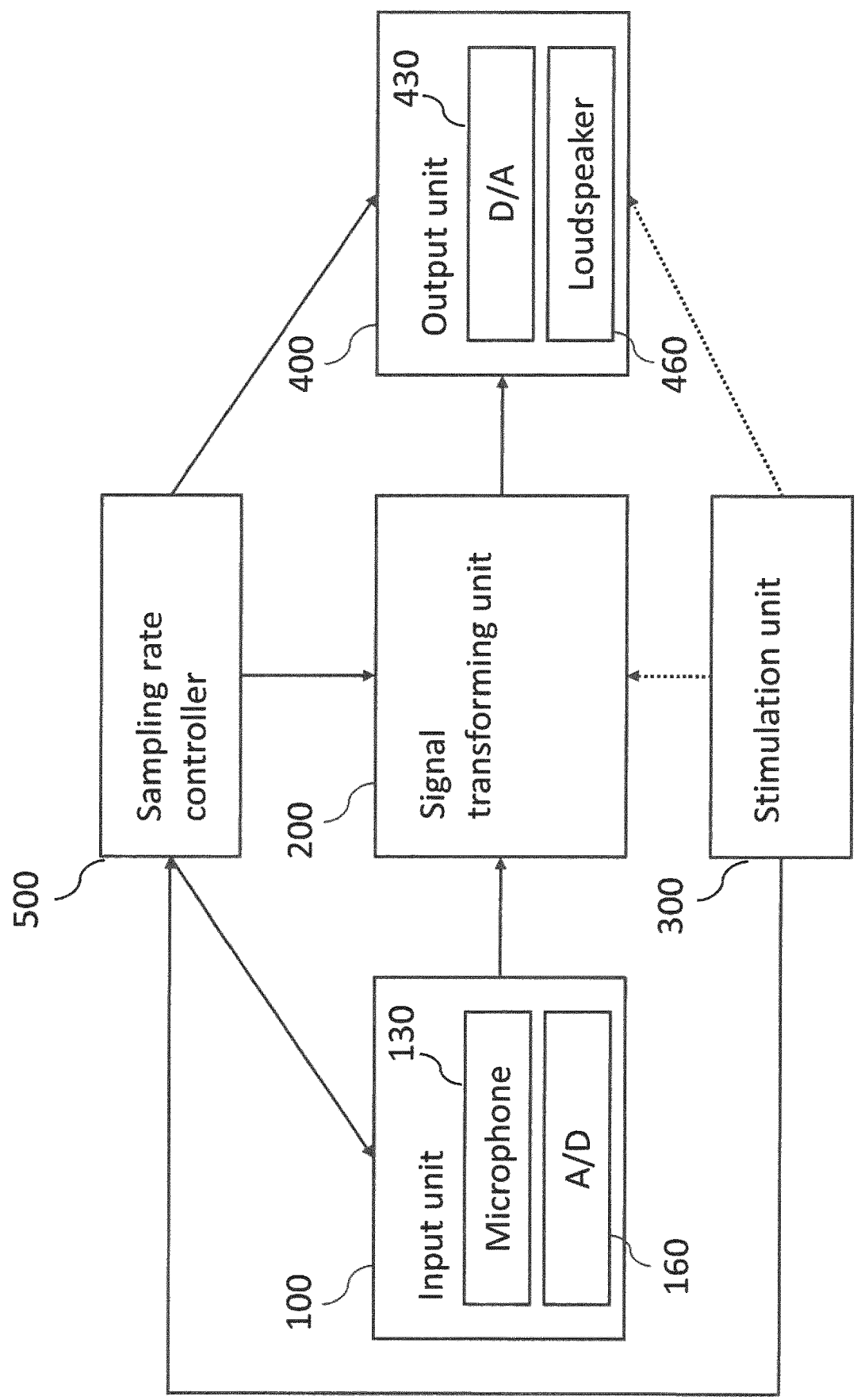
FIG. 1 shows a schematic representation of the components of an exemplary hearing aid device according to the invention.

The hearing aid device comprises an input unit 100 including a microphone 130 and an A/D converter 160, a signal transformation unit 200, a stimulation unit 300 and an output unit 400 including a D/A converter 430 and a loudspeaker 460. Each of the signal transformation unit 200 and stimulation unit 300 may include associated processing circuitry and programming that is operative to perform the functions recited herein. Further, each of the signal transformation unit 200 and stimulation unit 300 may include or may otherwise be coupled with an associated memory within which relevant programming data may be stored. The hearing aid device may further comprise other components not shown in FIG. 1, such as a battery configured to power the other components and a processing unit, such as a microprocessor, configured to control the operations of the other components. In some embodiments, at least the signal transformation unit 200 and stimulation unit 300 may be functional units of the microprocessor.

The input unit 100 of the hearing aid device receives an acoustical input from the environment surrounding the patient and transforms it into an electrical signal that can be further manipulated by the hearing aid device. Specifically, the microphone 130 turns the acoustical input into an analog electrical input signal, which is then converted by the A/D converter in a digital electrical input signal.

The signal transforming unit 200 receives the digital electrical input signal from the input unit 100. The signal transforming unit 200 modifies the digital electrical input signal to obtain an output signal, which is also a digital signal. The processing of the digital electrical input signal by the signal transforming unit 200 involves usually an amplification of the intensity of the signal in order to compensate for the hearing loss. Additionally or alternatively to the amplification, other modifications of the digital electrical input signal may be performed, such as noise suppression or filtering. Generally, the processing of the digital electrical input signal is performed on the basis of user data defining the specific hearing impairment in the user, e.g. the hearing threshold at given frequencies. These data may be stored in a memory within the hearing aid device, wherein the memory may be a component of the signal transforming unit itself or may be external to it.

The stimulation unit 300 generates stimulation signals suitable for acoustic CR neuromodulation therapy. In particular, the stimulation signal may be generated as a digital electrical signal that can be later converted into a sound, which is delivered to a patient in order to treat tinnitus. The stimulation unit 300 may generate one or more stimulation signals, wherein the different stimulation signals may have different characteristics, e.g. different frequencies. The one or more stimulation signals may be generated on the basis of data related to the tinnitus, such as tinnitus pitch, intensity and/or timbre. The tinnitus data may be stored in a memory within the hearing aid device, wherein the memory may be a component of the stimulation unit itself or may be external to it.

The digital electrical output signal produced by the signal transforming unit 200 and the digital stimulation signal generated by the stimulation unit 300 must then go through the output unit 400 in order to be delivered to the patient. In this respect, there may be two different implementations of the hearing aid device.

In a first example, both the signal transforming unit 200 and the stimulation unit 300 are coupled to the output unit 400. In other words, the signal transforming unit 200 sends the digital electrical output signal to the output unit 400 and the stimulation unit 300 sends the digital stimulation signal to the output unit 400.

In a second example, the stimulation unit 300 is coupled to the signal transforming unit 200 and the stimulation unit 300 sends the digital stimulation signal to the signal transforming unit 200, which may modify the digital stimulation signal. Then the transforming unit 200 sends the transformed digital stimulation signal to the output unit 400.

Irrespectively of the origin of the signals, the output unit 400 can receive the digital electrical output signal and the digital stimulation signal. It should be noted that the stimulation unit 300 does not generate stimulation signals at all times, so that the output unit 400 may receive only the digital electrical output signal at given moments. Similarly, if the patient finds him/herself in a quiet environment, the output unit 400 may receive only the digital stimulation signal. There may be cases in which the output unit 400 receives no signal. In any case, the output unit 400 is configured so that it is capable of receiving both signals at the same time.

The output unit 400 transforms at least one of the digital electrical output signal and the digital stimulation signal into an acoustical output, i.e. a sound wave. In particular, the D/A converter 430 converts the digital electrical output signal and/or the digital stimulation signal into respective analog signals. The loudspeaker 460 then transforms the analog electrical signal(s) into an acoustic wave.

Accordingly, the hearing aid device comprising the components shown in FIG. 1 functions both as a conventional hearing aid and as a CR neuromodulation therapy delivery device. To summarize, CR neuromodulation stimulation signals are not provided to the hearing aid by an external device such as an iPad or iPhone. Instead, the hearing aid electronic circuitry is itself adapted to provide high-frequency stimulation signals using, for example, internal programming capabilities and hardware configured to deliver high-frequency CR neuromodulation signals to the patient. Accordingly, the hearing aid device is configured to deliver: (a) high-frequency (e.g. 10 kHz and higher) CR neuromodulation stimulation signals to the patient, and (b) conventional (e.g. 10 kHz or less) audio signals to the patient. The stimulation unit 300 may be controlled by the processing unit for generating the stimulation signals. External programming signals from the health care provider or the patient can be used to adjust the stimulation regime applied to the patient. The hearing aid battery life is improved by the above-described hearing aid device.

If the patient wears two hearing aid devices, one for the left ear and one for the right ear, and the CR neuromodulation therapy is to be delivered in stereo mode, there may be an issue with the synchronization of the stimulation signals delivered to the left and right ears. In order to address this issue, a synchronization signal is used.

In one example, the first hearing aid device (master device) is configured to send the synchronization signal to the second hearing aid device (slave device). In particular, the synchronization signal is sent at fixed intervals in the time frame of the first hearing aid device, e.g. every second or every 10 second, and the slave device adjusts its operations on the basis of the timing coming from the master device.

In another example, the first hearing aid device and the second hearing aid device are configured to receive the synchronization signal from an external device. In this case, the synchronization signal may act as a calibration signal. The calibration signal may be sent twice to the hearing aid devices, with a predetermined time interval such as one second, between the first time and the second time. The hearing aid devices may be in a calibration mode, in which they measure how many clock cycles are contained in the predetermined time interval to obtain a calibration parameter. The calibration parameter may then be used when generating the stimulation signals with given frequencies.

Generating the stimulation signal within the hearing aid device leads to a diminished power consumption in comparison to streaming. However, when converting the stimulation signal in the output unit, a higher sampling rate is necessary to accurately reproduce high-frequency signals with respect to the conventional sampling rate of a hearing aid. Adopting this higher sampling rate is not efficient in terms of power.

A further reduction in the battery power consumption is achieved by using a variable sampling rate, which varies with time according to whether a stimulation signal is being generated and to its frequency components. Indeed, the higher sampling rate is only necessary when acoustic CR neuromodulation is applied through the hearing aid, specifically when the CR signals have frequency components higher than those usually processed by a conventional hearing aid.

Accordingly, a primary (low) sampling rate can be used when the hearing aid device performs only the function of a conventional hearing aid or when the generated stimulation signals have frequencies not exceeding a given threshold (primary threshold frequency), and a secondary (high) sampling rate can be used when the hearing aid device delivers the CR neuromodulation therapy using frequencies that exceed the threshold. The hearing aid device is, thus, configured to switch from a low sampling rate, e.g. about 16 kHz, to a high sampling rate, e.g. about 32 kHz, when required.

A sampling rate controller 500 may be used to set the primary or secondary sampling rate as sampling rate of the D/A converter 430. The sampling rate controller 500 may control the output sampling rate of the D/A converter 430 as well as the input sampling rate of the A/D converter 160. In particular, the input sampling rate may determine the primary sampling rate. Further, the sampling rate controller 500 may control the operations of the signal transforming unit 200. The sampling rate controller 500 is coupled to the stimulation unit 300 in order to receive information on the temporal schedule of the stimulation pattern.

Exemplarily, the chips Ezairo 7100 and Ezairo 7150 SL (company Semiconductors Components Industries, LLC) may be used to implement the functionality of a variable sampling rate.

Figure 2:
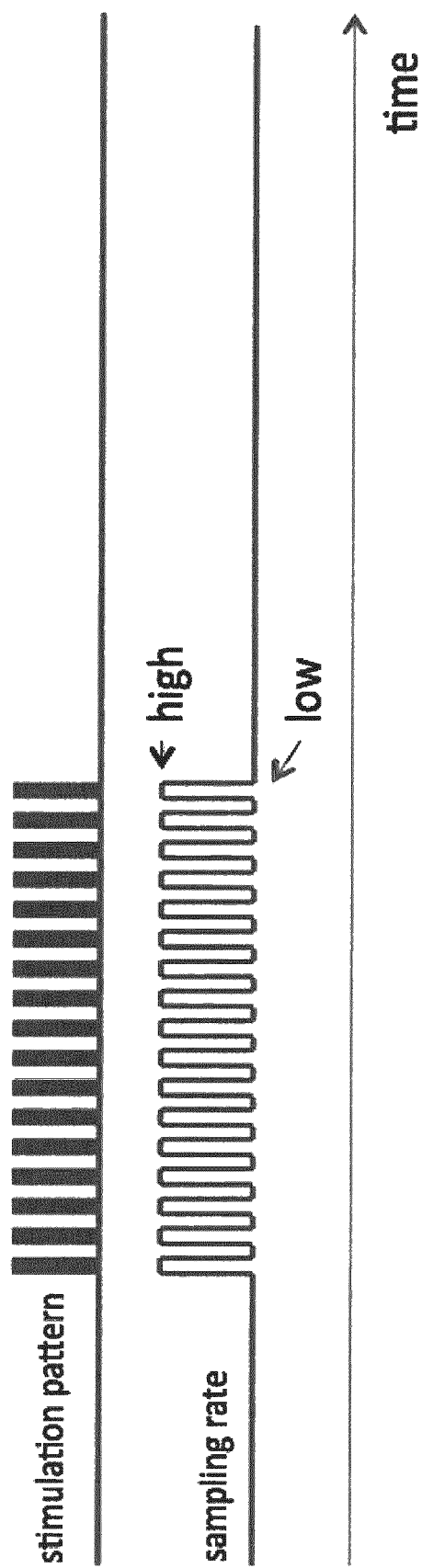
FIG. 2 shows an example of temporal variation of the sampling rate.

FIG. 2 shows the temporal variation of the sampling rate based on the stimulation pattern required by the CR neuromodulation, with stimulation signals having a frequency higher than the primary threshold frequency. The correspondence between the secondary (high) sampling rate and the occurrence of the stimulation is clearly seen in this figure. As an example, if acoustic CR neuromodulation is applied for 10 hours per day, the sampling rate needs to be increased to a high sampling rate state only during those periods when CR neuromodulation therapy is being delivered. Further, when pauses occur within those periods, the primary (low) sampling rate can be used again.

As explained above, higher sampling rates are necessary for signals having a frequency band extending to high frequencies. The frequency of the stimulation signals is determined based on the tinnitus pitch, which for most patients is around 8 kHz. For example, four monotone stimulation signals with four different frequencies may be delivered at different times, wherein the frequencies may be 6 kHz, 7 kHz, 9 kHz and 10 kHz. The primary (low) sampling rate may be adequate for reproducing the signals at 6 and 7 kHz, while the secondary (high) sampling rate may be necessary for the signals at 9 and 10 kHz. Accordingly, the primary threshold frequency may be set to 8 kHz.

Figure 3:
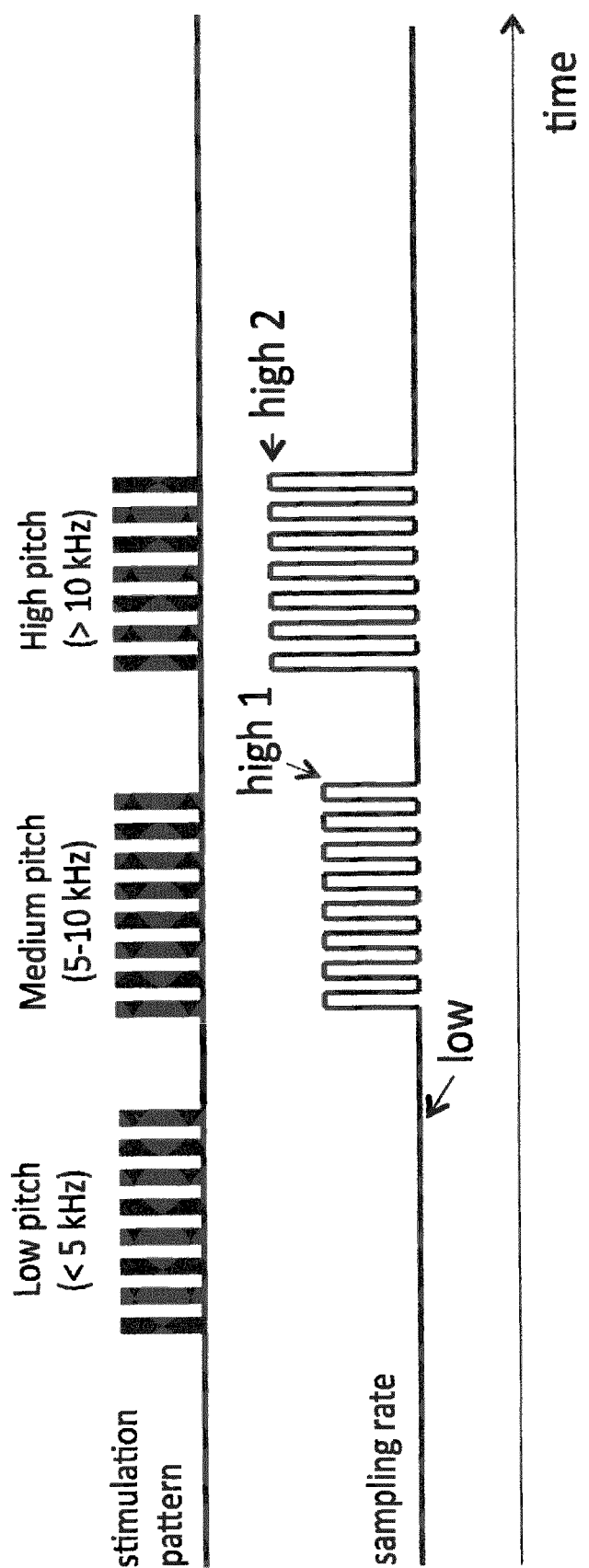
FIG. 3 shows another example of temporal variation of the sampling rate.

Of course the same principle can be applied identifying more than two different frequency intervals, wherein an appropriate sampling rate can be associated with each frequency interval. Accordingly, a secondary threshold frequency may be defined. FIG. 3 shows a temporal variation of the sampling rate that accounts for different frequency regimes for the stimulation signal. In this example, there are three frequency regimes for the stimulation pattern separated by a primary threshold frequency at about 5 kHz and a secondary threshold frequency at about 10 kHz. The sampling rate controller 500 can set the primary sampling rate (low), a first secondary sampling rate (high 1) and a second secondary sampling rate (high 2).

The use of an adaptive sampling rate based on the frequency of the stimulation signal can further improve the battery performance of the hearing aid device by lowering the power consumption.

In one example, an at least partially additional (i.e. parallel) sound pathway implementing the components used to apply acoustic CR neuromodulation may be provided in the hearing aid device. In accordance with this example, core functionality and components of the hearing aid may be untouched, and the dedicated additional audio pathway can be constructed such that acoustic CR neuromodulation can be optimally applied. The additional audio pathway only needs to be turned on when stimulation is applied. If the electronics or the device are configured to provide a proper sleep mode, during pauses in delivery of CR neurostimulation power consuming components can be set to sleep.

Figure 4:
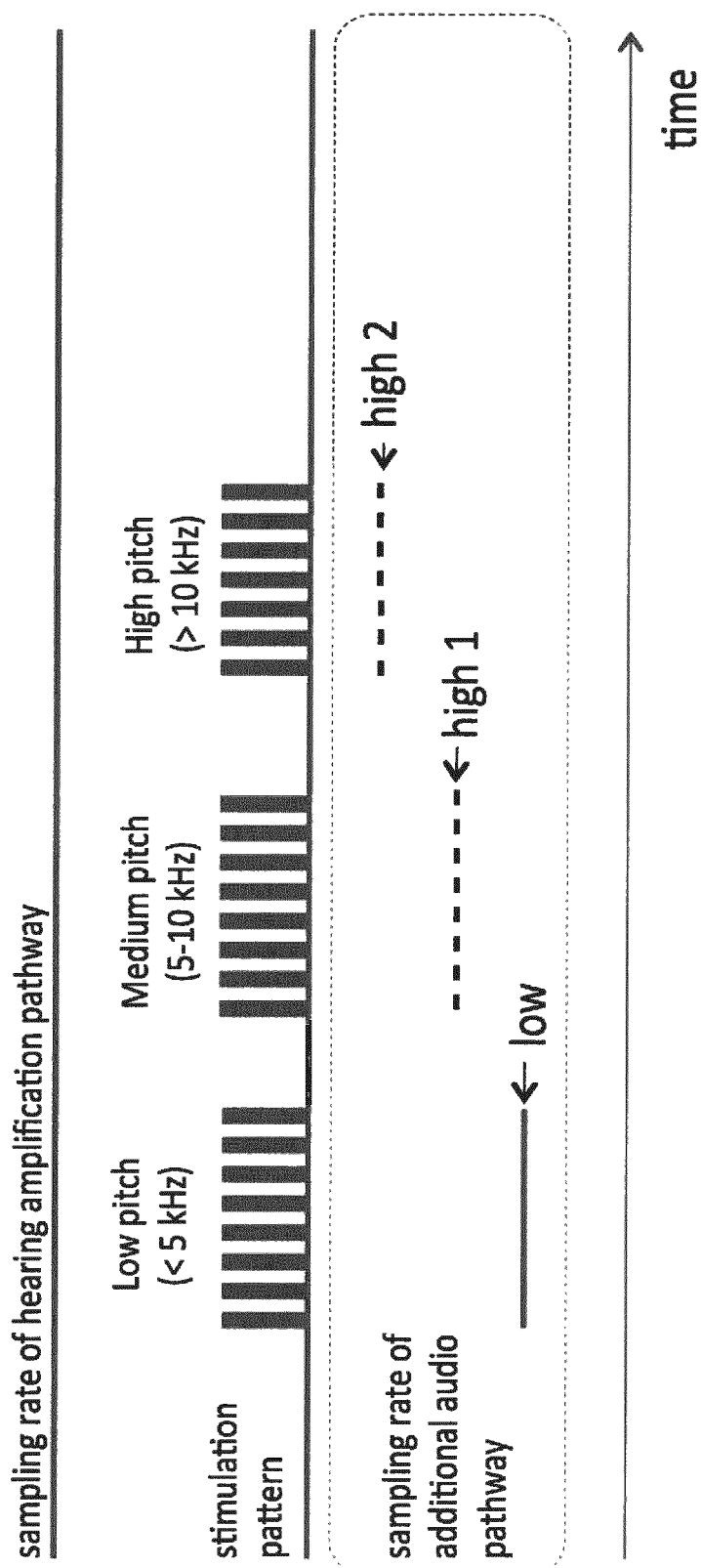
FIG. 4 shows an example of a variable sampling rate with an additional audio pathway.

Both components (i.e., hearing aid components and CR components) can use the same power source. FIG. 4 shows an example of a variable sampling rate, as in FIG. 3 but with an additional audio pathway.

In addition to the components shown in FIG. 1, the hearing aid device may comprise a tinnitus masker with high frequency noise to further stabilize any effects obtained with CR neuromodulation.

Further, in some examples, the loudspeaker 460 employed to deliver audio and CR neuromodulation signals to the patient by the hearing aid output unit may be adapted and configured to provide flatter and higher amplitude output signals at higher frequencies, using, for example, MEMS technology. Improved high-frequency response of the signal driving transducer in combination with improved high-frequency characteristics of the output amplifier providing the audio and CR neuromodulation signals to the signal driving transducer can provide much improved CR neuromodulation therapy to a patient, while also providing normal audio or hearing aid signals in the lower portion of the sound spectrum.

The invention claimed is:

1. A hearing aid device comprising:
an input unit configured to receive an acoustical input and transform it into an electrical input signal;
a signal transforming unit coupled to the input unit and configured to process the electrical input signal to obtain an electrical output signal;
a stimulation unit configured to generate a stimulation signal for acoustic coordinated reset neuromodulation therapy; and
an output unit configured to transform the electrical output signal and the stimulation signal into an acoustical output; wherein:
the stimulation unit is configured to generate the stimulation signal according to a temporal schedule defining primary stimulation periods, in which no stimulation signal is generated or in which the stimulation signal is generated having no frequency component higher than a primary threshold frequency, and secondary stimulation periods, in which the stimulation signal is generated with at least one frequency component higher than the primary threshold frequency; and
the hearing aid device further comprises a sampling rate controller configured to set an output sampling rate for the output unit selected from a plurality of sampling rates including at least a primary sampling rate and at least one secondary sampling rate higher than the primary sampling rate, wherein the sampling rate controller is configured to set the primary sampling rate as the output sampling rate during the primary stimulation periods and to set the at least one secondary sampling rate as the output sampling rate during the secondary stimulation periods.

2. The hearing aid device according to claim 1, wherein:
the secondary stimulation periods comprises at least first secondary stimulation periods, in which the stimulation signal is generated having no frequency component higher than a secondary threshold frequency, and second secondary stimulation periods, in which the stimulation signal is generated with at least one frequency component higher than the secondary threshold frequency;
the at least one secondary sampling rate comprises a first secondary sampling rate and a second secondary sampling rate; and
the sampling rate controller is configured to set the first secondary sampling rate as the output sampling rate during the first secondary stimulation periods and to set the second secondary sampling rate as the output sampling rate during the second secondary stimulation periods.

3. The hearing aid device according to claim 2, wherein the secondary threshold frequency is higher than about 5 kHz, preferably higher than about 6 kHz, more preferably higher than about 8 kHz, most preferably higher than about 10 kHz.

4. The hearing aid device according to claim 1, wherein the sampling rate controller is configured to set the primary sampling rate as an input sampling rate for the input unit.

5. The hearing aid device according to claim 1, wherein the primary sampling rate is not higher than about 30 kHz, preferably not higher than about 20 kHz, more preferably not higher than about 16 kHz, even more preferably not higher than about 12 kHz, most preferably not higher than about 10 kHz.

6. The hearing aid device according to claim 1, wherein the at least one secondary sampling rate is higher than about 12 kHz, preferably higher than about 16 kHz, more preferably higher than about 20 kHz, even more preferably higher than about 30 kHz, most preferably higher than about 40 kHz.

7. The hearing aid device according to claim 1, wherein the primary threshold frequency is not higher than about 10 kHz, preferably not higher than about 8 kHz, more preferably not higher than about 6 kHz, most preferably not higher than about 5 kHz.

8. The hearing aid device according to claim 1, wherein:
the stimulation unit is configured to generate the stimulation signal according to a temporal schedule defining passive stimulation periods, in which no stimulation signal is generated, and active stimulation periods, in which the stimulation signal is generated; and
the hearing aid device further comprises a clock cycle rate controller configured to set a clock cycle rate for the signal transforming unit selected from a plurality of clock cycle rates including at least a primary clock cycle rate and at least one secondary clock cycle rate higher than the primary clock cycle rate, wherein the clock cycle rate controller is configured to set the primary clock cycle rate as the clock cycle rate for the signal transforming unit during the passive stimulation periods and to set the at least one secondary clock cycle rate as the clock cycle rate for the signal transforming unit during the active stimulation periods.

9. A system comprising a first hearing aid device and a second hearing aid device, each of the first hearing aid device and second hearing aid device comprising:

an input unit configured to receive an acoustical input and transform it into an electrical input signal;
a signal transforming unit coupled to the input unit and configured to process the electrical input signal to obtain an electrical output signal;
a stimulation unit configured to generate a stimulation signal for acoustic coordinated reset neuromodulation therapy; and
an output unit configured to transform the electrical output signal and the stimulation signal into an acoustical output;
wherein the stimulation unit is configured to generate the stimulation signal according to a temporal schedule defining primary stimulation periods, in which no stimulation signal is generated or in which the stimulation signal is generated having no frequency component higher than a primary threshold frequency, and secondary stimulation periods, in which the stimulation signal is generated with at least one frequency component higher than the primary threshold frequency; and
further comprising a sampling rate controller configured to set an output sampling rate for the output unit selected from a plurality of sampling rates including at least a primary sampling rate and at least one secondary sampling rate higher than the primary sampling rate, wherein the sampling rate controller is configured to set the primary sampling rate as the output sampling rate during the primary stimulation periods and to set the at least one secondary sampling rate as the output sampling rate during the secondary stimulation periods
wherein the first hearing aid device is adapted for application to a left ear of a patient and the second hearing aid device is adapted for application to a right ear of the patient.

10. The system of claim 9, wherein the first hearing aid device is configured to send a synchronization signal to the second hearing aid device.

11. The system of claim 9, wherein the first hearing aid device and the second hearing aid device are configured to receive a synchronization signal from an external device.

12. A method for controlling a hearing aid device, the method comprising:
receiving, at an input unit of the hearing aid device, an acoustical input and transforming it into an electrical input signal;
processing, at a signal transforming unit of the hearing aid device coupled to the input unit, the electrical input signal to obtain an electrical output signal;
generating, at a stimulation unit of the hearing aid device, a stimulation signal for acoustic coordinated reset neuromodulation therapy; and
transforming, at an output unit of the hearing aid device, the electrical output signal and the stimulation signal into an acoustical output;
wherein the stimulation signal is generated according to a temporal schedule defining primary stimulation periods, in which no stimulation signal is generated or in which the stimulation signal is generated having no frequency component higher than a primary threshold frequency, and secondary stimulation periods, in which the stimulation signal is generated with at least one frequency component higher than the primary threshold frequency; and
the method further comprises setting an output sampling rate for the output unit selected from a plurality of sampling rates including at least a primary sampling rate and at least one secondary sampling rate higher than the primary sampling rate, wherein the primary sampling rate is set as the output sampling rate during the primary stimulation periods and the at least one secondary sampling rate is set as the output sampling rate during the secondary stimulation periods.

13. The method of claim 12, wherein the stimulation signal is generated according to a temporal schedule defining passive stimulation periods, in which no stimulation signal is generated, and active stimulation periods, in which the stimulation signal is generated; and the method further comprises setting a clock cycle rate for the signal transforming unit selected from a plurality of clock cycle rates including at least a primary clock cycle rate and at least one secondary clock cycle rate higher than the primary clock cycle rate, wherein the primary clock cycle rate is set as the clock cycle rate for the signal transforming unit during the passive stimulation periods and the at least one secondary clock cycle rate is set as the clock cycle rate for the signal transforming unit during the active stimulation periods.

* * * * *